US012715930B2

(12) United States Patent
Liang et al.

(10) Patent No.: US 12,715,930 B2
(45) **Date of Patent: *Aug. 25, 2026**

(54) USE OF ANTI-OX40 ANTIBODY IN TREATMENT OF TUMOR OR CANCER

(71) Applicant: Bio-Thera Solutions, Ltd., Guangzhou (CN)

(72) Inventors: Shizhong Liang, Guangzhou (CN); Binghui Liang, Guangzhou (CN); Jin-Chen Yu, Guangzhou (CN); Xiao Li, Guangzhou (CN); Shuqiang Song, Guangzhou (CN); Shengfeng Li, Guangzhou (CN)

(73) Assignee: BIO-THERA SOLUTIONS, LTD., Guangdong (CN)

(*) Notice: Subject to any disclaimer, the term of this patent is extended or adjusted under 35 U.S.C. 154(b) by 624 days.

This patent is subject to a terminal disclaimer.

(21) Appl. No.: 18/037,401

(22) PCT Filed: Nov. 18, 2021

(86) PCT No.: PCT/CN2021/131542

§ 371 (c)(1),
(2) Date: May 17, 2023

(87) PCT Pub. No.: WO2022/105839

PCT Pub. Date: May 27, 2022

(65) Prior Publication Data

US 2023/0416386 A1 Dec. 28, 2023

(30) Foreign Application Priority Data

Nov. 19, 2020 (CN) ......................... 202011301761.2

(51) Int. Cl.

*C07K 16/28* (2006.01)
*A61K 39/00* (2006.01)
*A61P 35/00* (2006.01)

(52) U.S. Cl.

CPC .......... *C07K 16/2878* (2013.01); *A61P 35/00* (2018.01); *A61K 2039/505* (2013.01); *C07K 2317/41* (2013.01); *C07K 2317/94* (2013.01)

(58) Field of Classification Search

CPC ............ C07K 16/2878; C07K 2317/41; C07K 2317/94; C07K 2317/33; C07K 2317/51; C07K 2317/515; C07K 2317/565; A61P 35/00; A61P 35/02; A61K 2039/505

See application file for complete search history.

(56) References Cited

U.S. PATENT DOCUMENTS

| | | | | |
|---|---|---|---|---|
| 8,283,450 B2 * | 10/2012 | Kato | A61P 21/00 530/387.3 |
| 2017/0182156 A1 | 6/2017 | Khleif | |
| 2018/0171023 A1 | 6/2018 | Harding | |
| 2023/0139700 A1 * | 5/2023 | Liang | A61P 35/00 424/143.1 |

FOREIGN PATENT DOCUMENTS

| | | | |
|---|---|---|---|
| CN | 113429483 A | 9/2021 |
| EP | 3126394 B1 | 10/2019 |
| EP | 4130039 A1 | 2/2023 |
| WO | 2017130076 A1 | 8/2017 |
| WO | 2020063660 A1 | 4/2020 |

OTHER PUBLICATIONS

Bittner, B., et al, Subcutaneous Administration of Biotherapeutics: An Overview of Current Challenges and Opportunities, BioDrugs (2018) 32:425-440 (Year: 2018).*

Redmond, W., et al, Challenges and opportunities in the development of combination immunotherapy with OX40 agonists, Expert Opin Biol Ther. Aug. 20, 2023;23(9):901-912, published Aug. 20, 2024. (Year: 2024).*

Wang, S. et al, Precision engineering of antibodies: A review of modification and design in the Fab region, International Journal of Biological Macromolecules, 275 (2024) 133730 (Year: 2024).*

Rudikoff, S., et al, Single amino acid substitution altering antigen-binding specificity, Proc. Natl. Acad. Sci., vol. 79, pp. 1979-1983, published Mar. 1982. (Year: 1982).*

Thapa, B., et al, OX40/OX40 ligand and its role in precision immune oncology, Cancer and Metastasis Reviews 43:1001-1013, published Mar. 25, 2024. (Year: 2024).*

Wang, R., et al, An Integrative Approach to Inform Optimal Administration of OX40 Agonist Antibodies in Patients with Advanced Solid Tumors, Clin Cancer Res 2019;25:6709-20, published Nov. 15, 2019 (Year: 2019).*

Buchan et al., "The immunobiology of CD27 and OX40 and their potential as targets for cancer immunotherapy," Blood, vol. 131, No. 1, pp. 39-48 (Jan. 4, 2018).

Gramaglia et al., "The OX40 Costimulatory Receptor Determines the Development of CD4 Memory by Regulating Primary Clonal Expansion," Journal of Immunology, 165:3043-3050 (2000).

International Search Report mailed on Feb. 18, 2022, in corresponding PCT/CN2021/131542.

Kuang et al., "Development and characterization of a novel anti-OX40 antibody for potent immune activation," Cancer Immunology, Immunotherapy, vol. 69, No. 6, pp. 939-950 (Published online Feb. 20, 2020).

Paterson et al., "Antigens Of Activated Rat T Lymphocytes Including A Molecule Of 50,000 Mr Detected Only On CD4 Positive T Blasts," Molecular Immunology, vol. 24, No. 12, pp. 1281-1290 (1987).

(Continued)

*Primary Examiner* — Bao-Thuy L Nguyen
*Assistant Examiner* — Bonirath Chhay
(74) *Attorney, Agent, or Firm* — Panitch Schwarze Belisario & Nadel LLP

(57) ABSTRACT

The use of an anti-OX40 antibody or an antigen-binding fragment in the treatment of a tumor or cancer, is described. Also described is a treatment method of a tumor or cancer and includes administering to a patient in need an effective amount of an anti-OX40 antibody or an antigen-binding fragment. Kits including an anti-OX40 antibody or an antigen-binding fragment are also described.

12 Claims, 1 Drawing Sheet

Specification includes a Sequence Listing.

(56) References Cited

OTHER PUBLICATIONS

Ward-Kavanagh et al., "The TNF Receptor Superfamily in Co-stimulating and Co-inhibitory Responses," Immunity Review, vol. 44, pp. 1005-1019 (May 17, 2016).
Willoughby et al., "OX40: Structure and function—What questions remain?," Molecular Immunology, vol. 83, pp. 13-22 (2017).
Aspeslagh et al., "Rationale for anti-OX40 cancer immunotherapy," European Journal of Cancer, vol. 52, pp. 50-66 (2016).
Extended European Search Report issued on Nov. 8, 2024, in EP Application No. 21893989.6.

* cited by examiner

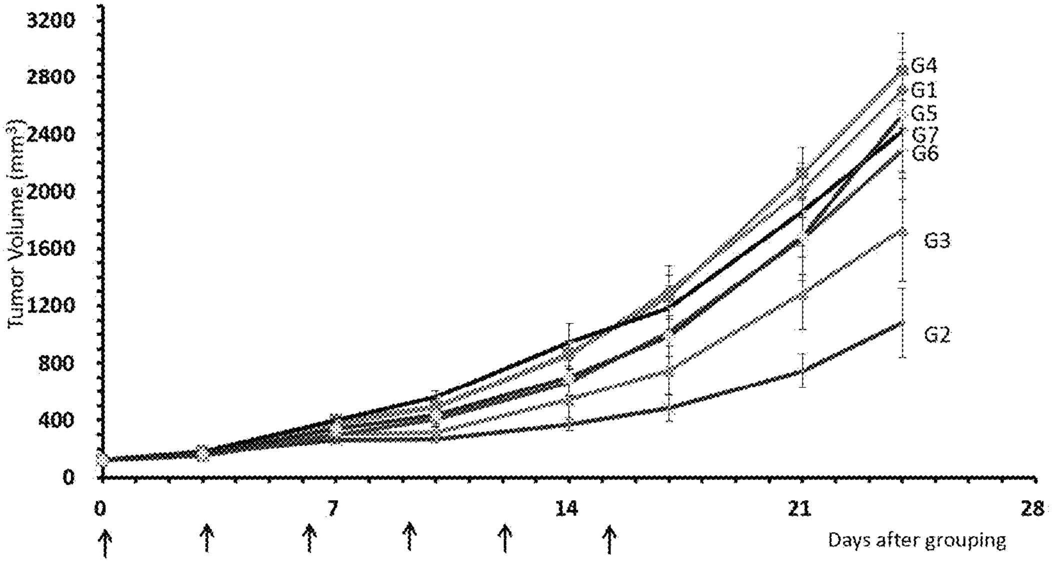
3200
2800
2400
2000
1600
1200
800
400
0
Tumor Volume (mm3)
0
7
14
21
28
Days after grouping
G4
G1
G5
G7
G6
G3
G2

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Ser Tyr Gly Met His
1               5


<210> SEQ ID NO 2
<211> LENGTH: 17
<212> TYPE: PRT
<213> ORGANISM: Artificial Sequence
<220> FEATURE:
<223> OTHER INFORMATION: synthetic construct

<400> SEQUENCE: 2

Val Ile Trp Glu Asp Gly Ser Asn Gln Tyr Tyr Ala Asp Ser Val Lys
1               5                   10                  15

Gly


<210> SEQ ID NO 3
<211> LENGTH: 13
<212> TYPE: PRT
<213> ORGANISM: Artificial Sequence
<220> FEATURE:
<223> OTHER INFORMATION: synthetic construct

<400> SEQUENCE: 3

Asp Asn Gln Asp Thr Ser Pro Asp Val Gly Ile Asp Tyr
1               5                   10


<210> SEQ ID NO 4
<211> LENGTH: 11
<212> TYPE: PRT
<213> ORGANISM: Artificial Sequence
<220> FEATURE:
<223> OTHER INFORMATION: synthetic construct

<400> SEQUENCE: 4

Arg Ala Ser Gln Asn Ile Ser Pro Phe Leu Asn
1               5                   10


<210> SEQ ID NO 5
```

<211> LENGTH: 7
<212> TYPE: PRT
<213> ORGANISM: Artificial Sequence
<220> FEATURE:
<223> OTHER INFORMATION: synthetic construct

<400> SEQUENCE: 5

```
Ala Ala Val Gly Leu Gln Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: synthetic construct

<400> SEQUENCE: 6

```
Gln Gln Tyr Thr Asp Tyr Pro Leu Thr
1               5
```

<210> SEQ ID NO 7
<211> LENGTH: 122
<212> TYPE: PRT
<213> ORGANISM: Artificial Sequence
<220> FEATURE:
<223> OTHER INFORMATION: synthetic construct

<400> SEQUENCE: 7

```
Gln Val Gln Leu Val Glu Ser Gly Gly Gly Val Val Gln Pro Gly Glu
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Glu Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Gln Asp Thr Ser Pro Asp Val Gly Ile Asp Tyr Trp
            100                 105                 110

Gly Gln Gly Thr Leu Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: synthetic construct

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Pro Phe
            20                  25                  30

Leu Asn Trp Tyr Gln Gln Lys Pro Gly Lys Ala Pro Lys Leu Leu Ile
        35                  40                  45

Tyr Ala Ala Val Gly Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Thr Asp Tyr Pro Leu
85 90 95

Thr Phe Gly Gly Gly Thr Lys Val Glu Ile Lys
100 105

<210> SEQ ID NO 9
<211> LENGTH: 452
<212> TYPE: PRT
<213> ORGANISM: Artificial Sequence
<220> FEATURE:
<223> OTHER INFORMATION: synthetic construct

<400> SEQUENCE: 9

Gln Val Gln Leu Val Glu Ser Gly Gly Gly Val Val Gln Pro Gly Glu
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Glu Asp Gly Ser Asn Gln Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Asn Gln Asp Thr Ser Pro Asp Val Gly Ile Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 10
<211> LENGTH: 214
<212> TYPE: PRT
<213> ORGANISM: Artificial Sequence
<220> FEATURE:
<223> OTHER INFORMATION: synthetic construct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Pro Phe
            20                  25                  30

Leu Asn Trp Tyr Gln Gln Lys Pro Gly Lys Ala Pro Lys Leu Leu Ile
        35                  40                  45

Tyr Ala Ala Val Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 1413
<212> TYPE: DNA
<213> ORGANISM: Artificial Sequence
<220> FEATURE:
<223> OTHER INFORMATION: synthetic construct

<400> SEQUENCE: 11
atggagttcg gactgagctg ggtgtttctg gtggccattc tgaaaggcgt gcagtgccaa 60
gtgcagctgg tggagagcgg aggaggagtg gtgcaacccg gcgagtccct cagactgagc 120
tgtgccgcca gcggcttcac cttcagctcc tacggcatgc actgggtgag acaagccccc 180
ggcaaaggac tggagtgggt ggccgtgatc tgggaggatg gctccaacca gtactatgcc 240
gacagcgtga agggaagatt caccatctct agagacaact ccaagaacac actgtatctg 300
cagatgaact ctctgagggc cgaggacacc gccgtgtact actgcgccaa ggacaaccaa 360
gacaccagcc ccgacgtggg catcgattat tggggccagg gtaccctggt taccgttagc 420
agcgcgagca ccaaaggccc gagcgtgttt ccgctggccc cgagcagcaa aagcaccagc 480
ggtggcaccg cagcgctggg ttgcctggtg aaagattatt tcccggaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacccag 660
acctacatct gcaacgtgaa tcacaagccc agcaacacca aggtggacaa gaaagttgag 720
cccaaatctt gtgacaaaac tcacacatgc ccaccgtgcc cagcacctga actcctgggg 780
ggaccgtcag tcttcctctt ccccccaaaa cccaaggaca ccctcatgat ctcccggacc 840
cctgaggtca catgcgtggt ggtggacgtg agccacgaag accctgaggt caagttcaac 900
tggtacgtgg acggcgtgga ggtgcataat gccaagacaa agccgcggga ggagcagtac 960
aacagcacgt accgtgtggt cagcgtcctc accgtcctgc accaggactg gctgaatggc 1020
aaggagtaca agtgcaaggt ctccaacaaa gccctcccag cccccatcga gaaaaccatc 1080
tccaaagcca aagggcagcc ccgagaacca caggtgtaca ccctgccccc atcccgggat 1140
gagctgacca agaaccaggt cagcctgacc tgcctggtca aaggcttcta tcccagcgac 1200
atcgccgtgg agtgggagag caatgggcag ccggagaaca actacaagac cacgcctccc 1260
gtgctggact ccgacggctc cttcttcctc tacagcaagc tcaccgtgga caagagcagg 1320
tggcagcagg ggaacgtctt ctcatgctcc gtgatgcatg aggctctgca caaccactac 1380
acgcagaaga gcctctccct gtctccgggt aaa 1413

<210> SEQ ID NO 12
<211> LENGTH: 708
<212> TYPE: DNA
<213> ORGANISM: Artificial Sequence
<220> FEATURE:
<223> OTHER INFORMATION: synthetic construct

<400> SEQUENCE: 12
atggacatga gagtgctggc tcagctgctg ggactgctgc tgctgtgctt tcccggcgcc 60
agatgcgaca tccagatgac ccagagccct agctctctgt ccgctagcgt gggagataga 120
gtgaccatca catgcagagc cagccagaac atctccccct ttctgaattg gtatcagcag 180
aagcccggca aggcccctaa gctgctgatc tatgccgctg tgggactgca gagcggagtg 240
ccttccagat tctccggcag cggcagcgga accgacttca cactgaccat cagctctctg 300

-continued

```
cagcccgagg acttcgccac ctactactgc cagcagtata ccgactaccc tctgaccttc    360

ggaggcggca ccaaggtgga gatcaagcgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgt                 708
```

USE OF ANTI-OX40 ANTIBODY IN TREATMENT OF TUMOR OR CANCER

CROSS-REFERENCE TO RELATED APPLICATIONS

This application is a Section 371 of International Application No. PCT/CN2021/131542, filed Nov. 18, 2021, which was published in the Chinese language on May 27, 2022 under International Publication No. WO 2022/105839 A1, which claims priority under 35 U.S.C. § 119(b) to International application No. 202011301761.2, filed Nov. 19, 2020, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689755_12US_Sequence_Listing", creation date of May 17, 2023, and having a size of 12,607 bytes. The sequence listing submitted via EFS-Web is part of the specification and is herein incorporated by reference in its entirety.

TECHNICAL FIELD

The present invention relates to the field of bio-pharmaceuticals, and particularly to use of an anti-OX40 antibody in the treatment of a tumor or cancer.

BACKGROUND

There are two types of checkpoints in the immune system. One is inhibitory, such as PD-1, and the other is activating, such as OX40. The complete activation of T cells in the immune system requires two levels of signals. The first signal is generated by the recognition of an antigen through a T cell antigen receptor, and the activation signal is transduced into a cell via a CD3 molecule. The second signal, known as a co-stimulatory signal, is generated by the interaction between co-stimulatory molecules on the surface of an antigen-presenting cell or a target cell and co-stimulatory molecule receptors on the surface of an activated T cell. The co-stimulatory signals promote proliferation of antigen-specific T cells and differentiation thereof into effector T cells (Lindsay K et al., *Immunity* 2016, 44(5): 1005-1019).

OX40, also known as TNFRSF4, ACT35, CD134, etc., belongs to the tumor necrosis factor receptor superfamily (TNFRSF), and is also a type I transmembrane glycoprotein. OX40 is not expressed on resting T cells but on activated $CD4^+$ T cells, $CD8^+$ T cells, NK cells and NKT cells (Paterson D J et al., *Mol. Immunol.*, 1987; 24: 1281-1290). T cells, after being activated by antigens, highly express OX40 molecules within 1-3 days, and the activation of OX40 signals may further enhance T cell activation signals to enhance immune system responses (Gramaglia I et al., *J. Immunol.* 2000; 165: 3043-3050).

At present, it is widely believed that the anti-OX40 antibody activates the immune system and inhibits tumors mainly through the following three cell physiological mechanisms. The first one is directly activating Teff cells of $CD4^+$ and $CD8^+$ to promote their proliferation and survival and the secretion of related inflammatory factors; as well as secretion of associated inflammatory factors; the second one is inhibiting the signals and activities of Treg cells to weaken their inhibitory effect on the immune system; the third one is depleting Treg cells by ADCC, ADCP or the like to reduce their suppression on Teff cells (J. Willoughby et al., *Molecular Immunology,* 83, 2017, 13-22).

OX40 is a very promising activating target in tumor immunotherapy and it can provide a new means for tumor immunotherapy.

SUMMARY

The present invention discloses a method or use of an anti-OX40 antibody or an antigen-binding fragment in the treatment of a tumor or cancer. In some embodiments, the anti-OX40 antibody or the antigen-binding fragment is for use in treating a tumor or cancer.

In some embodiments, the anti-OX40 antibody or the antigen-binding fragment comprises at least one or more of HCDR1 set forth in SEQ ID NO: 1, HCDR2 set forth in SEQ ID NO: 2, HCDR3 set forth in SEQ ID NO: 3, LCDR1 set forth in SEQ ID NO: 4, LCDR2 set forth in SEQ ID NO: 5, and LCDR3 set forth in SEQ ID NO: 6.

In some embodiments, the anti-OX40 antibody or the antigen-binding fragment comprises HCDR1 set forth in SEQ ID NO: 1, HCDR2 set forth in SEQ ID NO: 2, HCDR3 set forth in SEQ ID NO: 3, LCDR1 set forth in SEQ ID NO: 4, LCDR2 set forth in SEQ ID NO: 5, and LCDR3 set forth in SEQ ID NO: 6.

In some embodiments, the heavy chain variable region of the anti-OX40 antibody or the antigen-binding fragment comprises a sequence set forth in SEQ ID NO: 7, or a sequence having at least 80% identity to the sequence set forth in SEQ ID NO: 7, or an amino acid sequence having one or more conservative amino acid substitutions compared to the sequence set forth in SEQ ID NO: 7; and/or a light chain variable region of the anti-OX40 antibody or the antigen-binding fragment comprises a sequence set forth in SEQ ID NO: 8, a sequence having at least 80% identity to the sequence set forth in SEQ ID NO: 8, or an amino acid sequence having one or more conservative amino acid substitutions as compared to the sequence set forth in SEQ ID NO: 8.

In some embodiments, the heavy chain variable region of the anti-OX40 antibody or the antigen-binding fragment comprises a sequence set forth in SEQ ID NO: 7, and the light chain variable region of the anti-OX40 antibody or the antigen-binding fragment comprises a sequence set forth in SEQ ID NO: 8.

In some embodiments, a heavy chain of the anti-OX40 antibody comprises a sequence set forth in SEQ ID NO: 9, a sequence having at least 80% identity to the sequence set forth in SEQ ID NO: 9, or a sequence having one or more conservative amino acid substitutions as compared to the sequence set forth in SEQ ID NO: 9; and/or a light chain of the anti-OX40 antibody comprises a sequence set forth in SEQ ID NO: 10, a sequence having at least 80% identity to the sequence set forth in SEQ ID NO: 10, or an amino acid sequence having one or more conservative amino acid substitutions compared to the sequence set forth in SEQ ID NO: 10.

In some embodiments, the anti-OX40 antibody is antibody M or antibody M-KF, the heavy chain of antibody M or antibody M-KF comprises a sequence set forth in SEQ ID NO: 9, and the light chain of antibody M or antibody M-KF comprises a sequence set forth in SEQ ID NO: 10; antibody M or antibody M-KF comprises two heavy chains having the same sequence and two light chains having the same sequence.

In some embodiments, the anti-OX40 antibody (e.g., antibody M-KF) or the antigen-binding fragment has a fucosylation level of 0%-10%. In some embodiments, the anti-OX40 antibody (e.g., antibody M-KF) or the antigen-binding fragment has a fucosylation level of 0%-5%. In some embodiments, the anti-OX40 antibody (e.g., antibody M-KF) or the antigen-binding fragment has a fucosylation level of about 0%, about 0.1%, about 0.5%, about 0.8%, about 1%, about 1.3%, about 1.6%, about 2.1%, about 2.9%, about 3%, about 3.3%, about 3.8%, about 4%, about 4.2%, about 4.3%, about 4.6% or about 5%, or a range between any two of these values (inclusive) or any value therein. In some embodiments, the anti-OX40 antibody (e.g., antibody M-KF) or the antigen-binding fragment does not bind to fucose. In some embodiments, the anti-OX40 antibody (e.g., antibody M-KF) or the antigen-binding fragment has an enhanced ADCC (anti-dependent cell-mediated cytotoxicity) effect.

The anti-OX40 antibody or the antigen-binding fragment can be expressed in a CHO cell or a HEK293 cell by genetic engineering and obtained by purification; the purification can be performed by conventional methods, such as performing centrifugation on the cell suspension and collecting the supernatant, and then performing centrifugation again to further remove impurities. Protein A affinity column, ion exchange column and other methods can be used for purifying antibody protein.

In some embodiments, the anti-OX40 antibody or the antigen-binding fragment is expressed by a cell line in which an α-(1,6)-fucosyltransferase gene is knocked out, such as the CHO-BAT-KF cell line disclosed in PCT/CN2018/100008. In some embodiments, antibody M-KF is expressed by a CHO-BAT-KF cell line.

In some embodiments, the method or use comprises: administering to a patient in need thereof an effective amount of an anti-OX40 antibody or an antigen-binding fragment. In some embodiments, the anti-OX40 antibody is antibody M-KF. In some embodiments, antibody M-KF is expressed by a cell line in which an α-(1,6)-fucosyltransferase gene is knocked out. In some embodiments, the effective dose of the anti-OX40 antibody administered is about 0.6 mg to 900 mg per dose.

In some embodiments, the patient has a tumor or cancer. In some embodiments, the tumor and cancer include, but are not limited to, hematological cancer and solid tumor. In some embodiments, the hematologic cancer includes, but is not limited to, leukemia, lymphoma and myeloma. In some embodiments, the leukemia includes acute lymphocytic leukemia (ALL), acute myelogenous leukemia (AML), chronic lymphocytic leukemia (CLL), chronic myelogenous leukemia (CML), and myeloproliferative disorders (MPDs)/tumors. In some embodiments, the lymphoma includes Hodgkin's lymphoma, indolent and aggressive non-Hodgkin's lymphoma, Burkitt's lymphoma and follicular lymphoma (both small and large cell lymphomas). In some embodiments, the myeloma includes multiple myeloma (MM), giant cell myeloma, heavy chain myeloma, and light chain or Bence-Jones myeloma. In some embodiments, the solid tumor includes breast cancer, ovarian cancer, lung cancer, pancreatic cancer, prostate cancer, melanoma, colorectal cancer, lung cancer, head and neck cancer, bladder cancer, esophageal cancer, liver cancer and renal cancer. In some embodiments, the tumor and cancer are pathologically confirmed locally advanced or metastatic malignant solid tumors that have no effective treatment. In some embodiments, the present invention discloses a method for treating a tumor or cancer in a patient in need thereof comprising administering an effective amount of an anti-OX40 antibody or an antigen-binding fragment, wherein the effective amount of the anti-OX40 antibody or the antigen-binding fragment administered in each treatment cycle is about 0.6 mg to 900 mg. In some embodiments, one treatment cycle is 1 week, 2 weeks, 3 weeks, 4 weeks, 1 month, 5 weeks, 6 weeks, 7 weeks, or a range between any two of these values (inclusive) or any value therein. In some embodiments, the anti-OX40 antibody is antibody M-KF. In some embodiments, antibody M-KF is expressed by a cell line in which an α-(1,6)-fucosyltransferase gene is knocked out.

In some embodiments, the anti-OX40 antibody can be formulated into a pharmaceutical composition and administered to a patient in a variety of forms suitable for the chosen route of administration, such as parenteral, intravenous (iv), intramuscular, topical, or subcutaneous. In some embodiments, the anti-OX40 antibody can be intravenously infused. The dose of anti-OX40 antibody will depend on the properties of the drug, the extent to which the internalization, transport and release of the drug is triggered at the cell surface, and the disease being treated and the conditions of the patient (e.g., age, sex and body weight).

In some embodiments, the dose of the anti-OX40 antibody (e.g., antibody M or antibody M-KF) for each administration is about 0.01 mg/kg to 25 mg/kg, or a formulation containing the dose of the anti-OX40 antibody is administered. In some embodiments, the dose of the anti-OX40 antibody for each administration is about 0.01 mg/kg, about 0.02 mg/kg, about 0.03 mg/kg, about 0.06 mg/kg, about 0.08 mg/kg, about 0.1 mg/kg, about 0.2 mg/kg, about 0.3 mg/kg, about 0.5 mg/kg, about 0.9 mg/kg, about 1 mg/kg, about 2 mg/kg, about 2.5 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, or a range between any two of these values (inclusive) or any value therein, or a formulation containing the dose of the anti-OX40 antibody is administered. In some embodiments, the drug is administered about once every 1 week, about once every 2 weeks, about once every 3 weeks or about once every 4 weeks.

In some embodiments, the present invention discloses a method for treating a tumor or cancer, which comprises: administrating, every 3 weeks, to a patient in need thereof about 0.01 mg/kg, about 0.02 mg/kg, about 0.03 mg/kg, about 0.06 mg/kg, about 0.08 mg/kg, about 0.1 mg/kg, about 0.2 mg/kg, about 0.3 mg/kg, about 0.5 mg/kg, about 0.9 mg/kg, about 1 mg/kg, about 2 mg/kg, about 2.5 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg or about 25 mg/kg of the anti-OX40 antibody, or a formulation containing the dose of the anti-OX40 antibody.

In some embodiments, the present invention discloses a method for treating a tumor or cancer, which comprises: administrating, every 3 weeks, to a patient in need thereof about 0.01 mg/kg, about 0.02 mg/kg, about 0.03 mg/kg, about 0.06 mg/kg, about 0.08 mg/kg, about 0.1 mg/kg, about 0.2 mg/kg, about 0.3 mg/kg, about 0.5 mg/kg, about 0.9 mg/kg, about 1 mg/kg, about 2 mg/kg, about 2.5 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg or about 25 mg/kg of the anti-OX40 antibody M, or a formulation containing the dose of the anti-OX40 antibody M.

In some embodiments, the present invention discloses a method for treating a tumor or cancer, which comprises: administrating, every 3 weeks, to a patient in need thereof about 0.01 mg/kg, about 0.02 mg/kg, about 0.03 mg/kg, about 0.06 mg/kg, about 0.08 mg/kg, about 0.1 mg/kg, about 0.2 mg/kg, about 0.3 mg/kg, about 0.5 mg/kg, about 0.9 mg/kg, about 1 mg/kg, about 2 mg/kg, about 2.5 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg or about 25 mg/kg of the anti-OX40 antibody M-KF or a formulation containing the dose of the anti-OX40 antibody M-KF.

In some embodiments, the present invention discloses a method for treating a tumor or cancer comprising administering to a patient in need thereof an effective amount of an anti-OX40 antibody (or formulation); wherein the effective amount of the anti-OX40 antibody is about 0.6 mg to 900 mg (or a formulation containing the dose of the anti-OX40 antibody) in a single administration. The dosage schedule and administration route depend on benefit-risk assessment and general clinical practice guidelines for the anti-OX40 antibody (or formulation) in certain patient populations.

In some embodiments, the patient is administered the anti-OX40 antibody with an effective amount of about 0.6 mg and 900 mg (or a formulation containing the dose of the anti-OX40 antibody) per treatment cycle.

In some embodiments, the patient is administered the anti-OX40 antibody (e.g., antibody M or antibody M-KF) with an effective amount of about 0.6 mg, about 1 mg, about 1.8 mg, about 6 mg, about 10 mg, about 18 mg, about 30 mg, about 60 mg, about 100 mg, about 120 mg, about 180 mg, about 200 mg, about 250 mg, about 290 mg, about 300 mg, about 330 mg, about 380 mg, about 400 mg, about 434 mg, about 480 mg, about 500 mg, about 567 mg, about 580 mg, about 600 mg, about 700 mg, about 800 mg, about 900 mg, or a range between any two of these values (inclusive) or any value therein, or a formulation containing the dose of the anti-OX40 antibody per treatment cycle. In some embodiments, one treatment cycle is administering once every 1 week to 7 weeks. In some embodiments, the effective amount of the anti-OX40 antibody administered in each treatment cycle is about 0.6 mg to 600 mg, or a formulation containing the dose of the anti-OX40 antibody is administered; wherein one treatment cycle is about 1 week, about 2 weeks, about 3 weeks, about 4 weeks, about 5 weeks, about 6 weeks, about 7 weeks, or a range between any two of these values (inclusive) or any value therein. In some embodiments, one treatment cycle is about 1 week, about 2 weeks, about 3 weeks, or about 4 weeks. In some embodiments, the patient is administered the anti-OX40 antibody with an effective amount of about 0.6 mg to about 6 mg or a formulation containing the dose of the anti-OX40 antibody per treatment cycle; wherein one treatment cycle is about 1 week, about 2 weeks, about 3 weeks, or about 4 weeks. In some embodiments, the patient is administered the anti-OX40 antibody with an effective amount of about 0.6 mg, about 1 mg, about 1.5 mg, about 1.8 mg, about 2 mg, about 2.9 mg, about 3.6 mg, about 4 mg, about 4.3 mg, about 5 mg, about 5.5 mg, about 6 mg, or a range between any two of these values (inclusive) or any value therein or a formulation containing the dose of the anti-OX40 antibody per treatment cycle; wherein one treatment cycle is about 1 week, about 2 weeks, about 3 weeks, or about 4 weeks. In some embodiments, the patient is administered the anti-OX40 antibody with an effective amount of about 60 mg to 600 mg or a formulation containing the dose of the anti-OX40 antibody per treatment cycle; wherein one treatment cycle is about 1 week, about 2 weeks, about 3 weeks, or about 4 weeks. In some embodiments, the patient is administered the anti-OX40 antibody with an effective amount of about 60 mg, about 80 mg, about 90 mg, about 100 mg, about 120 mg, about 160 mg, about 180 mg, about 200 mg, about 243 mg, about 290 mg, about 355 mg, about 400 mg, about 425 mg, about 480 mg, about 500 mg, about 565 mg, about 600 mg, or a range between any two of these values (inclusive) or any value therein, or a formulation containing the dose of the anti-OX40 antibody per treatment cycle; wherein one treatment cycle is about 1 week, about 2 weeks, about 3 weeks, or about 4 weeks. In some embodiments, the patient is administered the anti-OX40 antibody with an effective amount of about 600 mg to 900 mg, or a formulation containing the dose of the anti-OX40 antibody per treatment cycle; wherein one treatment cycle is about 1 week, about 2 weeks, about 3 weeks, or about 4 weeks. In some embodiments, the patient is administered the anti-OX40 antibody with an effective amount of about 600 mg, about 680 mg, about 700 mg, about 750 mg, about 780 mg, about 800 mg, about 820 mg, about 900 mg, or a range between any two of these values (inclusive) or any value therein, or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 0.5 mg to 1 mg, or a formulation containing the dose of the anti-OX40 antibody per treatment cycle, such as administered about 0.6 mg once. In some embodiments, the patient is administered the anti-OX40 antibody with an effective amount of about 0.6 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 1.5 mg to 2.2 mg, or a formulation containing the dose of the anti-OX40 antibody per treatment cycle, such as administered about 1.8 mg once. In some embodiments, the patient is administered the anti-OX40 antibody with an effective amount of about 1.8 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 4 mg to 8 mg, or a formulation containing the dose of the anti-OX40 antibody per treatment cycle, such as administered about 6 mg once. In some embodiments, the patient is administered the anti-OX40 antibody with an effective amount of about 6 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 50 mg to 76 mg, or a formulation containing the dose of the anti-OX40 antibody per treatment cycle, such as administered about 60 mg once. In some embodiments, the patient is administered the anti-OX40 antibody with an effective amount of about 60 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 167 mg to 189 mg, or a formulation containing the dose of the anti-OX40 antibody per treatment cycle, such as administered about 180 mg once. In some embodiments, the patient is administered the anti-OX40 antibody with an effective amount of about 180 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 390 mg to 410 mg, or a formulation containing the dose of the anti-OX40 antibody per treatment cycle, such as administered about 400 mg once. In some embodiments, the patient is administered the anti-OX40 antibody with an effective amount of about 400 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 493 mg to 512 mg, or a formulation containing the dose of the anti-OX40 antibody per treatment cycle, such as administered about 500 mg once. In some embodiments, the patient is administered the anti-OX40 antibody with an effective amount of about 500 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 588 mg to 606 mg, or a formulation containing the dose of the anti-OX40 antibody per treatment cycle, such as administered about 600 mg once. In some embodiments, the patient is administered the anti-OX40 antibody with an effective amount of about 600 mg or a formulation containing the dose of the anti-OX40 antibody per treatment cycle; wherein one treatment cycle is about 1 week, about 2 weeks, about 3 weeks, or about 4 weeks.

In some embodiments, the patient is administered the anti-OX40 antibody (e.g., antibody M or M-KF) with an effective amount of about 882 mg to 916 mg, or a formulation containing the dose of the anti-OX40 antibody per treatment cycle, such as administered about 900 mg once. In some embodiments, the patient is administered the anti-OX40 antibody with an effective amount of about 900 mg or a formulation containing the dose of the anti-OX40 antibody per treatment cycle; wherein one treatment cycle is about 1 week, about 2 weeks, about 3 weeks, or about 4 weeks.

In some embodiments, the anti-OX40 antibody is administered at an effective amount of about 0.6 mg to 600 mg once every 3 weeks. In some embodiments, the anti-OX40 antibody is administered at an effective amount of about 0.6 mg, about 1.8 mg, about 6 mg, about 18 mg, about 60 mg, about 100 mg, about 180 mg, about 200 mg, about 300 mg, about 400 mg, about 500 mg, or about 600 mg once every 3 weeks. In some embodiments, the anti-OX40 antibody is administered at an effective amount of about 18 mg, about 60 mg or about 180 mg once every 3 weeks. In some embodiments, the anti-OX40 antibody is administered at an effective amount of about 600 mg to 900 mg once every 3 weeks. In some embodiments, the anti-OX40 antibody is administered at an effective amount of about 700 mg, about 800 mg or about 900 mg once every 3 weeks.

In some embodiments, the anti-OX40 antibody (or formulation) is administered to the patient once per treatment cycle. In some embodiments, the anti-OX40 antibody (or formulation) is administered multiple times, e.g., 2, 3, 4 or 5 times, per treatment cycle. In some embodiments, the patient is administered only 1 or 4 times per treatment cycle.

In some embodiments, the patient receives one treatment cycle of treatment. In some embodiments, the patient receives a plurality of (e.g., 2, 3, or 4) treatment cycles of treatment. In some embodiments, the patient receives treatment until the condition is alleviated and no treatment is required.

In some embodiments, the present invention discloses a method for treating a tumor or cancer, which comprises: administrating, every 3 weeks, to a patient in need thereof about 0.6 mg to 6 mg, about 6 mg to 60 mg, about 60 mg to 180 mg, about 180 mg to 600 mg, about 600 mg to 900 mg, e.g., about 0.6 mg, about 1.8 mg, about 6 mg, about 18 mg, about 60 mg, 100 mg, about 180 mg, about 200 mg, about 300 mg, about 400 mg, about 500 mg, about 600 mg or about 900 mg of the anti-OX40 antibody, or a formulation containing the dose of the anti-OX40 antibody. In some embodiments, the anti-OX40 antibody is antibody M. In some embodiments, the anti-OX40 antibody is antibody M-KF.

In some embodiments, about 0.6 mg of the anti-OX40 antibody is administered once every 3 weeks. In some embodiments, about 1.8 mg of the anti-OX40 antibody is administered once every 3 weeks. In some embodiments, about 6 mg of the anti-OX40 antibody is administered once every 3 weeks. In some embodiments, about 18 mg of the anti-OX40 antibody is administered once every 3 weeks. In some embodiments, about 60 mg of the anti-OX40 antibody is administered once every 3 weeks. In some embodiments, about 180 mg of the anti-OX40 antibody is administered once every 3 weeks. In some embodiments, about 600 mg of the anti-OX40 antibody is administered once every 3 weeks. In some embodiments, about 900 mg of the anti-OX40 antibody is administered once every 3 weeks.

In some embodiments, the patient is relieved of symptoms after a single dose is administered. In some embodiments, after a single dose is administered, the patient's symptoms have not been relieved as expected, and then about 0.6 mg to 900 mg of the anti-OX40 antibody is administered to the patient until the patient's symptoms have been relieved.

In some embodiments, the anti-OX40 antibody (or formulation) is administered by subcutaneous (s.c.) injection, intraperitoneal (i.p.) injection, parenteral injection, intra-arterial injection, intravenous (i.v.) injection, or the like. In some embodiments, the anti-OX40 antibody (or formulation) is administered by infusion. In some embodiments, the anti-OX40 antibody (or formulation) is administered by bolus injection.

In some embodiments, the anti-OX40 antibody (or formulation) is administered by intravenous infusion (i.e., i.v. infusion). In some embodiments, the intravenous infusion duration is about 50 minutes, about 55 minutes, about 60 minutes, about 65 minutes, about 70 minutes, about 75 minutes, about 81 minutes, about 87 minutes, about 90 minutes, about 95 minutes, or a range between any two of these values (inclusive) or any value therein. In some embodiments, the intravenous infusion duration is greater than or equal to 60 minutes.

In some embodiments, the anti-OX40 antibody (or formulation) is used in combination with other treatment methods for the treatment of a tumor or cancer, e.g., chemotherapy, radiotherapy, immunotherapy, hormonal therapy, targeted therapy, biological therapy and surgical therapy. In some embodiments, the anti-OX40 antibody (or formulation) is used in combination with other tumor or cancer therapeutic agents for the treatment of a tumor or cancer, e.g., a hormone and an antibody treating a tumor or cancer.

In another aspect, the present invention discloses use of an anti-OX40 antibody in the preparation of a medicament for treating a tumor or cancer. In some embodiments, the medicament for treating a tumor or cancer comprises an anti-OX40 antibody. In some embodiments, the anti-OX40 antibody is antibody M. In some embodiments, the anti-OX40 antibody is antibody M-KF. In some embodiments, antibody M-KF is expressed by a cell line in which an α-(1,6)-fucosyltransferase gene is knocked out.

In another aspect, the present invention also discloses a kit comprising an anti-OX40 antibody (or formulation) and an instruction for directing administration of the anti-OX40 antibody (or formulation) to a patient in need thereof. In some embodiments, the anti-OX40 antibody is antibody M. In some embodiments, the anti-OX40 antibody is antibody M-KF. In some embodiments, antibody M-KF is expressed by a cell line in which an α-(1,6)-fucosyltransferase gene is knocked out.

In another aspect, the present invention also discloses a pharmaceutical composition which comprises an anti-OX40 antibody and is suitable for injection, e.g., a bolus injection or infusion (drip) pharmaceutical composition. The pharmaceutical composition suitable for injection includes a sterile aqueous solution (herein water-soluble solution) or dispersion and sterile powders for the instant preparation of a sterile injectable solution or dispersion. For intravenous administration, a suitable carrier includes normal saline, bacteriostatic water or phosphate-buffered saline (PBS), ethanol, a solvent or dispersion medium for polyol (e.g., glycerol, propylene glycol and liquid polyethylene glycol), and a suitable mixture thereof. In some embodiments, the pharmaceutical composition further comprises a pharmaceutically acceptable carrier. In some embodiments, the pharmaceutically acceptable carrier may include an antibacterial and/or antifungal agent, e.g., p-hydroxylbenzoate, chlorobutanol, phenol, ascorbic acid and thimerosal. In some embodiments, the pharmaceutically acceptable carrier may include an isotonic agent, such as a sugar, a polyol (such as mannitol and sorbitol), and sodium chloride. In some embodiments, the pharmaceutical composition comprises at least 0.1% anti-OX40 antibody. The percentage of antibody may vary and is between about 2% and 90% by weight of a given dosage form. The amount of anti-OX40 antibody in such a therapeutically useful pharmaceutical composition may be an effective amount for administration. In some embodiments, the anti-OX40 antibody is antibody M. In some embodiments, the anti-OX40 antibody is antibody M-KF. In some embodiments, antibody M-KF is expressed by a cell line in which an α-(1,6)-fucosyltransferase gene is knocked out.

In another aspect, the present invention also discloses a method for preparing the pharmaceutical composition described above: mixing the anti-OX40 antibody described herein with a pharmaceutically acceptable carrier suitable for injection (e.g., water for injection and normal saline). The method for mixing the anti-OX40 antibody described above with the pharmaceutically acceptable carrier is generally known in the art.

The anti-OX40 antibody (or formulation) of the present invention can be used for treating a tumor or cancer.

BRIEF DESCRIPTION OF THE DRAWINGS

FIG. 1 shows that anti-OX40 antibody M-KF inhibits the proliferation of tumor cells; the ordinate represents tumor volume.

TERMS

Unless otherwise specified, each of the following terms shall have the meaning described below.

Definitions

It should be noted that the term "an" entity refers to one or more of the entities. For example, "an antibody" should be interpreted as one or more antibodies. As such, the terms "a" (or "an"), "one or more" and "at least one" can be used interchangeably herein.

The term "polypeptide" is intended to encompass both the singular form "polypeptide" and the plural form "polypeptides", and refers to a molecule consisting of amino acid monomer linearly linked by amide bonds (or peptide bonds). The term "polypeptide" refers to any single chain or multiple chains of two or more amino acids and does not refer to a particular length of the product. Thus, included within the definition of "polypeptide" are peptides, dipeptides, tripeptides, oligopeptides, "proteins", "amino acid chains", or any other term used to refer to chains of two or more amino acids, and the term "polypeptide" may be used in place of, or interchangeably with, any of the above terms. The term "polypeptide" is also intended to refer to a product of post-expression polypeptide modification, including but not limited to glycosylation, acetylation, phosphorylation, amidation, derivatization by known protecting/blocking groups, proteolytic cleavage or non-naturally occurring amino acid modification. The polypeptide may be derived from a natural biological source or produced by recombinant techniques, but it is not necessarily translated from a specified nucleic acid sequence, and it may be produced in any manner, including chemical synthesis.

"Amino acid" refers to an organic compound containing both an amino group and a carboxyl group, such as an α-amino acid that can be encoded by a nucleic acid, either directly or in the form of a precursor. A single amino acid is encoded by a nucleic acid consisting of three nucleotides (so-called codon or base triplet). Each amino acid is encoded by at least one codon. The same amino acid is encoded by different codons, which is known as "codon degeneracy". Amino acids include natural amino acids and non-natural amino acids. Natural amino acids include alanine (three-letter code: Ala, one-letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

"Conservative amino acid substitution" refers to the substitution of one amino acid residue with another amino acid residue having a side chain (R group) of similar chemical nature (e.g., charge or hydrophobicity). Generally, conservative amino acid substitutions do not substantially alter the functional properties of the protein. Examples of amino acid classes with a side chain of similar chemical nature include: 1) an aliphatic side chain: glycine, alanine, valine, leucine and isoleucine; 2) an aliphatic hydroxyl side chain: serine and threonine; 3) an amide-containing side chain: asparagine and glutamine; 4) an aromatic side chain: phenylalanine, tyrosine and tryptophan; 5) a basic side chain: lysine, arginine and histidine; and 6) an acidic side chain: aspartic acid and glutamic acid.

A number of amino acids of "conservative amino acid substitutions of VL or VH" may be about 1, about 2, about 3, about 4, about 5, about 6, about 8, about 9, about 10, about 11, about 13, about 14, about 15 conservative amino acid substitutions, or a range between any two of these values (inclusive) or any value therein. A number of amino acids of "conservative amino acid substitutions of a heavy chain or a light chain" may be about 1, about 2, about 3, about 4, about 5, about 6, about 8, about 9, about 10, about 11, about 13, about 14, about 15, about 18, about 19, about 22, about 24, about 25, about 29, about 31, about 35, about 38, about 41, about 45 conservative amino acid substitutions, or a range between any two of these values (inclusive) or any value therein.

The term "encoding" as applied to a polynucleotide refers to a polynucleotide known to "encode" a polypeptide. When in its native state or manipulated by methods well known to those skilled in the art, the polypeptide and a fragment thereof can be produced by transcript and/or translation.

The term "recombinant", with regard to a polypeptide or polynucleotide, is intended to refer to a polypeptide or polynucleotide that does not occur in nature, and non-limiting examples can be combined to produce a polynucleotide or polypeptide that does not normally occur.

"Identity" refers to sequence similarity between two peptides or between two nucleic acid molecules. Homology can be determined by comparing the positions that can be aligned in the sequences. When a position of the compared sequences is occupied by the same base or amino acid, then the molecules are homologous at that position. The degree of homology between the sequences is a function of the number of matching or homologous positions shared by the sequences.

"At least 80% identity" refers to about 80% identity, about 81% identity, about 82% identity, about 83% identity, about 85% identity, about 86% identity, about 87% identity, about 88% identity, about 90% identity, about 91% identity, about 92% identity, about 94% identity, about 95% identity, about 98% identity, about 99% identity, or a range between any two of these values (inclusive) or any value therein.

A polynucleotide or a polynucleotide sequence (or a polypeptide or an antibody sequence) having a certain percentage (e.g., 90%, 95%, 98% or 99%) of "identity or sequence identity" to another sequence refers to that when the sequences are aligned, the percentage of bases (or amino acids) in the sequence are the same. This alignment identity percentage or sequence identity can be determined using visual inspection or software programs known in the art, such as the software programs described in Ausubel et al. eds., (2007), *Current Protocols in Molecular Biology*. Preferably, the alignment is performed using default parameters. One alignment program is BLAST using default parameters, such as BLASTN and BLASTP, both using the following default parameters: Genetic code=standard; filter=none; strand=both; cutoff=60; expect=10; Matrix=BLOSUM62; Descriptions=50 sequences; sort by=HIGH SCORE; Databases=non-redundant; GenBank+EMBL+DDBJ+PDB+GenBank CDS translations+SwissProtein+SPupdate+PIR. Biologically equivalent polynucleotides are polynucleotides having the above-specified percentage identity and encoding polypeptides having identical or similar biological activity.

"Antibody" or "antigen-binding fragment" refers to a polypeptide or polypeptide complex that specifically recognizes and binds to an antigen. The antibody may be an intact antibody and any antigen-binding fragment or single chain thereof. The term "antibody" thus includes any protein or peptide comprising at least a portion of an immunoglobulin molecule that has biological activity for binding to an antigen. The antibody and the antigen-binding fragment include, but are not limited to, complementarity determining regions (CDRs) of a heavy or light chain or a ligand binding portion thereof, heavy chain variable regions (VHs), light chain variable regions (VLs), heavy chain constant regions (CHs), light chain constant regions (CLs), framework regions (FRs) or any portion thereof, or at least a portion of a binding protein. The CDRs include light chain CDRs (LCDR1-3) and heavy chain CDRs (HCDR1-3).

The term "antibody" includes a wide variety of polypeptides that can be biochemically distinguished. Those skilled in the art will appreciate that the classes of heavy chains include gamma, mu, alpha, delta, or epsilon (γ, μ, α, δ, or ε), and some subclasses (e.g., γ1-γ4). The nature of this chain determines the "type" of the antibody as IgG, IgM, IgA, IgD or IgE. Immunoglobulin subclasses (isotypes), such as IgG1, IgG2, IgG3, IgG4, IgG5, etc., have been well characterized and the functional specificity imparted is also known. All types of immunoglobulins are within the scope of the present invention. In some embodiments, the immunoglobulin molecule is an IgG species. These four chains are connected in a "Y" configuration through disulfide bonds, wherein the light chain starts at the opening of "Y" configuration and extends through the variable region to surround the heavy chain.

Antibodies, antigen-binding fragments or derivatives disclosed herein include, but are not limited to, polyclonal, monoclonal, multispecific, fully human, humanized, primatized or chimeric antibodies, single-chain antibodies, epitope-binding fragments (e.g., Fab, Fab' and $F(ab')_2$), and scFv.

Light chains can be classified into kappa (κ) or lambda (λ). Each heavy chain may bind to a κ or λ light chain. In general, when an immunoglobulin is produced by a hybridoma, a B cell or a genetically engineered host cell, the light and heavy chains are bound by covalent bonds, and the "tail" portions of the two heavy chains are bound by covalent disulfide bonds or non-covalent bonds. In the heavy chains, the amino acid sequence extends from the N terminus at the forked end of the Y configuration to the C terminus at the bottom of each chain. The immunoglobulin κ light chain variable region is $V_\kappa$; the immunoglobulin λ light chain variable region is $V_\lambda$.

Both the light and heavy chains are divided into structurally and functionally homologous regions. The terms "constant" and "variable" are used in accordance with function. The light chain variable region (VL) and heavy chain variable region (VH) determine the antigen recognition and specificity. The light chain constant region (CL) and the heavy chain constant region (CH) impart important biological properties such as secretion, transplacental movement, Fc receptor binding, complement fixation, etc. By convention, the numbering of amino acids in the constant regions increases as they become further away from the antigen-binding site of the antibody or amino terminus. The N-terminal portion is the variable region, and the C-terminal portion is the constant region; the CH3 and CL domains actually comprise the carboxyl termini of the heavy chain and light chain, respectively.

Where the terms used and/or accepted in the art have two or more definitions, the definitions of the terms used herein include all of these meanings unless explicitly indicated as opposite. One specific example is the use of the term "complementarity determining regions" ("CDRs") to describe non-contiguous antigen-binding sites found within the variable regions of heavy and light chain polypeptides. This specific region is described in Kabat et al., U.S. Dept. of Health and Human Services, *Sequences of Proteins of Immunological Interest* (1983) and Chothia et al., *J. Mol. Biol.* 196:901-917 (1987), which are incorporated herein by reference in their entireties.

CDRs defined according to Kabat and Chothia schemes include overlaps or subsets of amino acid residues when compared to each other. Nevertheless, it is within the scope of the present invention to apply any definition to refer to the CDRs of an antibody or a variant thereof. The exact number of residues comprising a specific CDR will vary according to the sequence and size of the CDR. Those skilled in the art can generally determine which specific residues a CDR comprises based on the variable region amino acid sequence of an antibody.

Kabat et al. also define a numbering system applicable to the variable region sequence of any antibody. One of ordinary skills in the art can apply the "Kabat numbering" system to any variable region sequence without depending on other experimental data beyond the sequence itself. "Kabat numbering" refers to the numbering system proposed by Kabat et al., U.S. Dept. of Health and Human Services in *Sequence of Proteins of Immunological Interest* (1983). EU or Chothia numbering system can be also applicable to the antibody.

"Treatment" refers to both therapeutic treatment and prophylactic or preventative measures, the purpose of which is to prevent, slow down, ameliorate, and halt undesirable physiological changes or disorders, such as the progression of a disease, including, but not limited to, alleviation of symptoms, diminishment of extent of disease, stabilized (i.e., not worsening) state of disease, delay or slowing of disease progression, amelioration or palliation of the disease state, alleviation or elimination (whether partial or total), prolonged survival compared to expected survival without treatment, and the like, as either detectable or undetectable. Patients in need of treatment include patients already with a condition or disorder, patients susceptible to a condition or disorder, or patients in need of prevention of the condition or disorder, or patients who may or are expected to benefit from administration of the antibody or the composition disclosed herein for detection, diagnostic procedures, and/or treatment.

"Patient" refers to any mammal in need of diagnosis, prognosis or treatment, including humans, dogs, cats, guinea pigs, rabbits, rats, mice, horses, cattle and the like.

"About" refers to a general error range for corresponding values as readily understood by those skilled in the relevant art. In some embodiments, "about" mentioned herein refers to the values described and ranges thereof of ±10%, ±5%, or ±1%.

"Effective amount" refers to the amount of an active compound or medicament that results in a biological or medical response in a tissue, system, animal, individual, or human; the effective amount is sought by researchers, vets, doctors or other clinical doctors.

As used herein, the term "in need" means that the patient has been identified as in need of a particular method or treatment. In some embodiments, identification may be made by any diagnostic mode. The patient may be in need of any methods and treatments described herein.

The DNA encoding the antibody can be designed and synthesized according to the antibody amino acid sequence described herein by conventional methods, inserted into an expression vector, and transfected into a host cell. The transfected host cell is then cultured in a medium to produce the monoclonal antibody. In some embodiments, the vector expressing the antibody comprises at least one promoter element, an antibody coding sequence, a transcription termination signal and a polyA tail. Other elements include enhancers, Kozak sequences, and donor and recipient sites flanking the inserted sequence for RNA splicing. Efficient transcription can be obtained by early and late promoters of SV40, long terminal repeats from retroviruses such as RSV, HTLV1 and HIVI, and early promoters of cytomegalovirus, and promoters from other cells such as actin promoter can also be used. Suitable expression vectors may include pIRES1neo, pRetro-Off, pRetro-On, PLXSN, or Plncx, pcDNA3.1 (+/−), pcDNA/Zeo (+/−), pcDNA3.1/Hygro (+/−), PSVL, PMSG, pRSVcat, pSV2dhfr, pBC12MI, pCS2, etc. Commonly used mammalian cells include 293 cells, Cos1 cells, Cos7 cells, CV1 cells, murine L cells, CHO cells and the like.

DETAILED DESCRIPTION

The technical schemes of the present invention will be further illustrated below through specific examples, which are not intended to limit the protection scope of the present invention. Some nonessential modifications and adjustments made by other people according to the concept of the present invention still fall within the protection scope of the present invention.

The materials, reagents, and the like used in the following examples can be commercially available unless otherwise stated.

Example 1: Preparation Method for Antibodies

The DNA sequences of the light and heavy chains were constructed according to the amino acid sequences of the heavy and light chains of the antibody. The 5' and 3' terminuses of the DNA sequences were modified with PCR primers designed to add an appropriate leader sequence to each strand, and then the resulting sequences were cloned to the existing recombinant antibody expression vector. It was determined, by sequencing assay, that the recombinant plasmid was correctly constructed. The recombinant plasmid was transferred into expression cells for expression, and the supernatant was collected and purified to obtain an antibody protein sample which was used for the following various examples.

Wherein, 1) in the preparation process of the antibody M-KF, the expression vector used was pCDNA3.1™ (+) (Invitrogen company, the product number is V79020), the expression cells were CHO-BAT-KF cells, and the fucosylation level was 0 through testing; 2) the sequences of the heavy and light chains of the positive control antibody 11D4 were from Patent U.S. Pat. No. 8,236,930B2, the expression vector used was pCHO1.0 plasmid (purchased from Invitrogen), and the expression cells were CHO-S cells (purchased from Invitrogen). The amino acid sequences of antibody M-KF are shown in Table 1, the nucleic acid sequences of antibody M-KF are shown in Table 2, and the sequence of the leader peptide (i.e., leader sequence) is shown in the frame in Table 2.

TABLE 1

Amino acid sequences of antibody M and antibody M-KF (as divided by Kabat)

| Name | SEQ ID NO | Amino acid sequence |
|---|---|---|
| HCDR1 | 1 | SYGMH |
| HCDR2 | 2 | VIWEDGSNQYYADSVKG |
| HCDR3 | 3 | DNQDTSPDVGIDY |
| LCDR1 | 4 | RASQNISPFLN |
| LCDR2 | 5 | AAVGLQS |
| LCDR3 | 6 | QQYTDYPLT |
| VH | 7 | QVQLVESGGGVVQPGESLRL<br>SCAASGFTFSSYGMHWVRQA<br>PGKGLEWVAVIWEDGSNQYY<br>ADSVKGRFTISRDNSKNTLY<br>LQMNSLRAEDTAVYYCAKDN<br>QDTSPDVGIDYWGQGTLVTV<br>SS |
| VL | 8 | DIQMTQSPSSLSASVGDRVT<br>ITCRASQNISPFLNWYQQKP<br>GKAPKLLIYAAVGLQSGVPS<br>RFSGSGSGTDFTLTISSLQP<br>EDFATYYCQQYTDYPLTFGG<br>GTKVEIK |
| heavy chain | 9 | QVQLVESGGGVVQPGESLRL<br>SCAASGFTFSSYGMHWVRQA<br>PGKGLEWVAVIWEDGSNQYY<br>ADSVKGRFTISRDNSKNTLY<br>LQMNSLRAEDTAVYYCAKDN<br>QDTSPDVGIDYWGQGTLVTV<br>SSASTKGPSVFPLAPSSKST<br>SGGTAALGCLVKDYFPEPVT<br>VSWNSGALTSGVHTFPAVLQ<br>SSGLYSLSSVVTVPSSSLGT<br>QTYICNVNHKPSNTKVDKKV<br>EPKSCDKTHTCPPCPAPELL<br>GGPSVFLFPPKPKDTLMISR<br>TPEVTCVVVDVSHEDPEVKF<br>NWYVDGVEVHNAKTKPREEQ<br>YNSTYRVVSVLTVLHQDWLN<br>GKEYKCKVSNKALPAPIEKT<br>ISKAKGQPREPQVYTLPPSR<br>DELTKNQVSLTCLVKGFYPS<br>DIAVEWESNGQPENNYKTTP<br>PVLDSDGSFFLYSKLTVDKS<br>RWQQGNVFSCSVMHEALHNH<br>YTQKSLSLSPGK |
| light chain | 10 | DIQMTQSPSSLSASVGDRVT<br>ITCRASQNISPFLNWYQQKP<br>GKAPKLLIYAAVGLQSGVPS<br>RFSGSGSGTDFTLTISSLQP<br>EDFATYYCQQYTDYPLTFGG<br>GTKVEIKRTVAAPSVFIFPP<br>SDEQLKSGTASVVCLLNNFY<br>PREAKVQWKVDNALQSGNSQ<br>ESVTEQDSKDSTYSLSSTLT<br>LSKADYEKHKVYACEVTHQG<br>LSSPVTKSFNRGEC |

TABLE 2

Nucleic acid sequences of antibody M and antibody M-KF

| Name | SEQ ID NO | Nucleic acid sequence |
|---|---|---|
| heavy chain | 11 | **atg**gagttcggactgagctgggtgtttctggtggccattctgaaaggcgtgcagtgccaagtgcagctggtggaga<br>gcggaggaggagtggtgcaacccggcgagtccctcagactgagctgtgccgccageggcttcaccttcagctcct<br>acggcatgcactgggtgagacaagcccccggcaaaggactggagtgggtggccgtgatctgggaggatggctcc<br>aaccagtactatgccgacagcgtgaagggaagattcaccatctctagagacaactccaagaacacactgtatctgca<br>gatgaactctctgagggccgaggacaccgccgtgtactactgcgccaaggacaaccaagacaccagccccgacgt<br>gggcatcgattattggggccagggtaccctggttaccgttagcagcgcgagcaccaaaggcccgagcgtgtttccg<br>ctggccccgagcagcaaaagcaccagcggtggcaccgcagcgctgggttgcctggtgaaagattatttcccggaa<br>ccggtgacggtgtcgtggaactcaggcgccctgaccagcggcgtgcacaccttcccggctgtcctacagtcctcag<br>gactctactccctcagcagcgtggtgaccgtgccctccagcagcttgggcacccagacctacatctgcaacgtgaat<br>cacaagcccagcaacaccaaggtggacaagaaagttgagcccaaatcttgtgacaaaactcacacatgcccaccgt<br>gcccagcacctgaactcctggggggaccgtcagtcttcctcttccccccaaaacccaaggacaccctcatgatctcc<br>cggacccctgaggtcacatgcgtggtggtggacgtgagccacgaagaccctgaggtcaagttcaactggtacgtgg<br>acggcgtggaggtgcataatgccaagacaaagccgcgggaggagcagtacaacagcacgtaccgtgtggtcagc<br>gtcctcaccgtcctgcaccaggactggctgaatggcaaggagtacaagtgcaaggtctccaacaaagccctcccag<br>cccccategagaaaaccatctccaaagccaaagggcagccccgagaaccacaggtgtacaccctgcccccatccc<br>gggatgagctgaccaagaaccaggtcagcctgacctgcctggtcaaaggcttctatcccagcgacatcgccgtgga<br>gtgggagagcaatgggcagccggagaacaactacaagaccacgcctcccgtgctggactccgacggctccttctt<br>cctctacagcaagctcaccgtggacaagagcaggtggcagcaggggaacgtcttctcatgctccgtgatgcatgag<br>gctctgcacaaccactacacgcagaagagcctctccctgtctccgggtaaa |
| light chain | 12 | **atg**gacatgagagtgctggctcagctgctgggactgctgctgctgttgctttcccggcgccagatgcgacatccagat<br>gacccagagccctagctctctgtccgctagcgtgggagatagagtgaccatcacatgcagagccagccagaacatc<br>tccccctttctgaattggtatcagcagaagcccggcaaggcccctaagctgctgatctatgccgctgtgggactgcag<br>agcggagtgccttccagattctccggcageggcageggaaccgacttcacactgaccatcagctctctgcagcccg<br>aggacttcgccacctactactgccagcagtataccgactaccctctgaccttcggaggcggcaccaaggtggagatc |

TABLE 2-continued

| Nucleic acid sequences of antibody M and antibody M-KF | | |
|---|---|---|
| Name | SEQ ID NO | Nucleic acid sequence |
| | | aagcgtacggtggctgcaccatctgtcttcatcttcccgccatctgatgagcagttgaaatctggaactgcctctgttgt gtgcctgctgaataacttctatcccagagaggccaaagtacagtggaaggtggataacgccctccaatcgggtaact cccaggagagtgtcacagagcaggacagcaaggacagcacctacagcctcagcagcaccctgacgctgagcaa agcagactacgagaaacacaaagtctacgcctgcgaagtcacccatcagggcctgagctcgcccgtcacaaagag cttcaacaggggagagtgt |

Example 2: In-Vitro Pharmacodynamic Experiment

1) Tumor Inoculation

The anti-tumor efficacy of antibody M-KF of the present invention was studied in OX40 humanized mouse models (purchased from Biocytogen). MC38 tumor cells were seeded subcutaneously on the right side of OX40 humanized female mice at a concentration of $5\times10^5$ cells/0.1 mL.

2) Grouping and Administration

The mice were randomly grouped (6 mice per group) by tumor volume when tumors grew to 119 $mm^3$. The day of grouping was defined as D0, and the administration was started on D0; the grouping and dosing regimen is shown in Table 3, with the dosing dates of day 0, day 3, day 6, day 9, day 12, and day 15. The antibody was administered intraperitoneally at a frequency of Q3D (once every 3 days) at three dose groups of 1 mg/kg, 0.2 mg/kg and 0.04 mg/kg for a total of 6 administration. The dosing regimen is shown in Table 3.

3) Experimental Observation and Data Acquisition

After cell inoculation, the effect of tumors on the normal behavior of animals was routinely monitored weekly; specific indicators include activity, food and water intake, body weight gain or loss, the eyes, the hair coat and other abnormal conditions in the mice. The tumor volume and body weight were measured twice a week throughout the study, and the mice were euthanized when the tumors reached an endpoint or when the mice had more than 20% of body weight loss. The tumor volume ($mm^3$) was 0.5× (long diameter of tumor×short diameter of tumor$^2$).

4) Statistics

The tumor volume, mouse body weight, tumor weight, etc. of each group of mice were expressed as mean±standard error (mean±SEM). Data were analyzed using SPSS. $P<0.05$ means that there was a significant difference.

TGItv (inhibition rate for relative tumor volume) calculation formula was as follows:

$$TGItv=(1-(\text{mean } RTV_{dose\ group})/(\text{mean } RTV_{control\ group}))\times100\%;$$ mean $RTV_{dose\ group}$: mean RTV for dose group, mean $RTV_{control\ group}$: mean RTV for control group;

wherein $RTV_n=V_{nt}/V_{n0}$; $V_{nt}$: tumor volume at day t for mice numbered n, $V_{n0}$: tumor volume at day 0 for mice numbered n, and $RTV_n$: relative tumor volume at day t for mice numbered n.

TABLE 3

| Dosing regimen | | | | | | |
|---|---|---|---|---|---|---|
| Group | N | Dose group | Dose (mg/kg) | Route | Frequency | Number of actual administration |
| G1 | 6 | hIgG (Sino Biological Inc., product number: HG1K) | 1 | i.p. | Q3D | 6 times |
| G2 | 6 | Antibody M-KF | 1 | i.p. | Q3D | 6 times |
| G3 | 6 | Antibody M-KF | 0.2 | i.p. | Q3D | 6 times |
| G4 | 6 | Antibody M-KF | 0.04 | i.p. | Q3D | 6 times |
| G5 | 6 | Antibody 11D4 | 1 | i.p. | Q3D | 6 times |
| G6 | 6 | Antibody 11D4 | 0.2 | i.p. | Q3D | 6 times |
| G7 | 6 | Antibody 11D4 | 0.04 | i.p. | Q3D | 6 times |

Note:
N is the number of animals.

As shown in FIG. 1 and Table 4, the medium and high doses of antibody M-KF significantly inhibited the tumor growth ($P<0.05$), and the effect of antibody M-KF was significantly better than that of antibody 11D4 with a high dose; no significant difference was found in the body weight of the mice between the groups, indicating that antibody M-KF was well tolerated in mice.

TABLE 4

| Inhibition rate of tumor volume at day 24 | | | |
|---|---|---|---|
| Group | Tumor volume ($mm^3$) | TGItv (%) | P value |
| G1 (control) | 2708 ± 269 | — | — |
| G2 | 1083 ± 242 | 62.8 | 0.001 |
| G3 | 1732 ± 361 | 37.7 | 0.048 |
| G4 | 2844 ± 271 | −5.2 | 0.728 |
| G5 | 2536 ± 394 | 6.6 | 0.724 |
| G6 | 2291 ± 344 | 16.1 | 0.356 |
| G7 | 2422 ± 291 | 11.0 | 0.483 |

Example 3: Pharmacokinetic and Toxicology Experiment

1) Experimental design: the doses of antibody M-KF are 0.5 mg/kg, 2.5 mg/kg and 10 mg/kg, with 6 cynomolgus monkeys (3 males and 3 females)/group, a total of 18 monkeys; single intravenous infusion.

a) Pharmacokinetics

The whole blood was collected before administration (0 h) and 2 min, 2 h, 6 h, 12 h, 24 h, 48 h, 72 h, 96 h, 120 h, 168 h, 240 h, 336 h, 408 h, 504 h and 672 h after administration, and the sera were separated; the concentration of drug in each sample was analyzed using a validated ELISA method with a lower limit of quantification of 30 ng/mL.

The pharmacokinetic parameters in the sera of the animals in each group were statistically shown in Table 5, and after intravenous infusion of the antibody, the concentration of antibody M-KF in the sera rapidly peaked and declined in a roughly biphasic manner; the exposure of antibody M-KF (mean $C_{max}$ and mean $AUC_{0-4}$) increased with increasing dose, and the increase rate was comparable to the increase rate of the dose.

TABLE 5

Pharmacokinetic parameters for single administration in serum of animals of each group

| Dose (mg/kg) | Gender | | $t_{1/2}$ (h) | $T_{max}$ (h) | $C_{max}$ (μg/mL) | $AUC_{0-t}$ (h*μg/mL) | Vd (mL/kg) | CL (mL/h/kg) |
|---|---|---|---|---|---|---|---|---|
| 0.5 | Female | Mean | 213 | 0.033 | 15.3 | 2320 | 64.7 | 0.238 |
| | | SD | 135 | 0 | 0.529 | 778 | 26.8 | 0.0988 |
| | Male | Mean | 216 | 0.689 | 10.7 | 1460 | 108 | 0.347 |
| | | SD | 35.6 | 1.14 | 2.61 | 175 | 26.2 | 0.0389 |
| | All | Mean | 215 | 0.361 | 13 | 1890 | 86.6 | 0.292 |
| | | SD | 88 | 0.803 | 3.04 | 691 | 33.7 | 0.0898 |
| 2.5 | Female | Mean | 219 | 0.033 | 72.9 | 11900 | 79.1 | 0.226 |
| | | SD | 119 | 0 | 1.89 | 3960 | 67.9 | 0.0761 |
| | Male | Mean | 409 | 0.033 | 88.6 | 12000 | 127 | 0.21 |
| | | SD | 207 | 0 | 18.6 | 1210 | 71 | 0.0201 |
| | All | Mean | 314 | 0.033 | 80.7 | 12000 | 103 | 0.218 |
| | | SD | 183 | 0 | 14.6 | 2620 | 67.5 | 0.0506 |
| 10 | Female | Mean | 182 | 0.689 | 305 | 57900 | 49.3 | 0.185 |
| | | SD | 55.6 | 1.14 | 28 | 17500 | 25.6 | 0.061 |
| | Male | Mean | 188 | 0.689 | 335 | 48900 | 60.4 | 0.208 |
| | | SD | 177 | 1.14 | 54.7 | 7720 | 62.1 | 0.0307 |
| | All | Mean | 185 | 0.689 | 320 | 53400 | 54.8 | 0.196 |
| | | SD | 117 | 1.02 | 42.2 | 13100 | 42.9 | 0.045 |

b) Toxicity Evaluation

All animals were dissected and observed on day 30. No death or moribundity was found across all groups during the experiment, and there was no abnormal change which was definitely related to the test sample in the clinical observation, the body weight, the food consumption, blood coagulation, and blood plasma biochemistry of each group of animals.

The cynomolgus monkeys were administered antibody M-KF (0.5 mg/kg, 2.5 mg/kg or 10 mg/kg) by a single intravenous infusion, which was well tolerated without obvious toxic reaction in each dose group, and hence the maximum tolerated dose (MTD) was more than 10 mg/kg.

c) Immunogenicity

After intravenous infusion of antibody M-KF (0.5 mg/kg, 2.5 mg/kg or 10 mg/kg), individual positive rates were 100% (6/6), 100% (6/6) and 83.3% (5/6), respectively, and the overall positive rate for cynomolgus monkeys was 94.4% (17/18).

d) Receptor Occupancy

Blood was collected once each on day −1 (0 h), day 2 (24 h±1 h after administration), day 8 and day 29. The samples were analyzed using flow cytometry.

OX40 receptor occupancy on T lymphocytes ($CD3^+$ and $CD3^+$ $CD4^+$) for each dose group was near saturation on day 2 (RO rate>80%), and remained in saturation on day 8; on day 29, the (2.5 mg/kg and 10 mg/kg) dose groups maintained receptor occupancy saturation, while the (0.5 mg/kg) dose group decreased to about 20%, which was essentially the same as before administration (day −1).

2) Experimental design: the administration was intravenous infusion of antibody M-KF (1 mg/kg, 5 mg/kg and 30 mg/kg) or a vehicle, once every week for 5 times in total, followed by 4-week recovery after discontinuation; the administration was performed on day 1, day 8, day 15, day 22 and day 29; there were 10 cynomolgus monkeys per group (5 males and 5 females), a total of 40 monkeys; after the end of administration, 24 cynomolgus monkeys (3 males and 3 females per group) were euthanized, and the remaining 16 cynomolgus monkeys (2 males and 2 females per group) were euthanized after the end of the recovery period. During the experiment, the following indicators were evaluated: clinical observation, ophthalmologic examination, body weight, food consumption, body temperature, hematology, blood coagulation, blood plasma biochemistry, immunoglobulin, lymphocyte immunophenotype, urine, macroscopic morphological observation, organ weight, and histopathological examination.

a) Toxicity Evaluation

The cynomolgus monkeys were administered antibody M-KF (1 mg/kg, 5 mg/kg or 30 mg/kg) by intravenous infusion once every week with a total of 5 times continuously, and males and females were well tolerated at each dose, and a decrease in NEUT (the percentage of neutrophile granulocytes), a transient increase of IL-6, and slight histological changes in spleen/liver were seen mainly in each dose group; therefore, the highest non-severely toxic dose (HNSTD) for this experiment was considered to be 30 mg/kg.

b) Toxicokinetics

All samples to be analyzed were analyzed using a validated ELISA method. As shown in Table 6, the drug concentration of sera in most animals of each dose group rapidly peaked (2 min post-dose) after administration on days 1 and day 22, except for individual animals; on day 1, the mean $C_{max}$ and mean $AUC_{0-4}$ of the males and females both increased with increasing dose, and the increase rate was comparable to the increase rate of the dose, with no significant difference between the males and females.

TABLE 6

Toxicokinetic parameters for repeat administration

| | | Day 1 (first administration) | | | | | Day 22 ($4^{th}$ administration) | | | |
|---|---|---|---|---|---|---|---|---|---|---|
| Dose (mg/kg) | Gender | Mean $T_{max}$ (h) | Mean $C_{max}$ (ng/mL) | $C_{max}$ Ratio | Mean $AUC_{0-t}$ (h*ng/mL) | $AUC_{0-t}$ Ratio | Mean $T_{max}$ (h) | Mean $C_{max}$ (ng/mL) | Mean $AUC_{0-t}$ (h*ng/ml) | AR |
| 1 | M | 0.0333 | 27200 | 1.0 | 2850000 | 1.0 | 0.0333 | 1430 | 1550 | — |
| | F | 0.827 | 25800 | 1.0 | 2930000 | 1.0 | 0.0333 | 15100 | 1460000 | — |
| | All | 0.430 | 26500 | 1.0 | 2890000 | 1.0 | 0.0333 | 8240 | 728000 | — |
| 5 | M | 0.0333 | 147000 | 5.4 | 14500000 | 5.1 | 1.62 | 166000 | 17900000 | — |
| | F | 0.0333 | 140000 | 5.4 | 13800000 | 4.7 | 0.0333 | 56400 | 1220000 | — |
| | All | 0.0333 | 144000 | 5.4 | 14200000 | 4.9 | 0.827 | 111000 | 9570000 | — |
| 30 | M | 0.827 | 910000 | 33.5 | 93100000 | 32.7 | 3.22 | 1560000 | 178000000 | 1.9 |
| | F | 0.0333 | 862000 | 33.4 | 86800000 | 29.6 | 0.0333 | 1730000 | 213000000 | 2.5 |
| | All | 0.430 | 886000 | 33.4 | 90000000 | 31.1 | 1.62 | 1650000 | 195000000 | 2.2 |

Note:
$C_{max}$ ratio = mean $C_{max}$/mean $C_{max}$ in the 1 mg/kg dose group;
$AUC_{0-t}$ ratio = mean $AUC_{0-t}$/$AUC_{0-t}$ in the 1 mg/kg dose group;
the accumulation ratio AR = mean $AUC_{0-t}$ on day 22/mean $AUC_{0-t}$ on day 1.

c) Immunogenicity

The serum samples were collected using a validated ECLA assay (electrochemiluminescence immunoassay for immunogenicity): after repeated intravenous infusions of antibody M-KF (1 mg/kg, 5 mg/kg or 30 mg/kg), the individual positive rates were 90.0% (9/10), 80.0% (8/10) and 20.0% (2/10), respectively, and the overall positive rate of the animals after administration was 63.3% (19/30).

d) Local Stimulation by Administration

After the cynomolgus monkeys were administered antibody M-KF (1 mg/kg, 5 mg/kg or 30 mg/kg) by intravenous infusion for 4 weeks continuously, no local stimulation reaction related to the test sample was found at the administration part of the animals in each dose group.

Example 3: In-Vitro Hemolysis Experiment and Tissue Cross-Reactivity Experiment

Through the use of human red blood cells as a test model, when the antibody M-KF injection (25.8 mg/mL) was diluted more than 10-fold, the hemolysis or blood coagulation of human red blood cells would not occur in vitro.

5 μg/mL and 40 μg/mL of antibody M-KF did not cross-react with the tissues of human and cynomolgus monkeys with the immunohistochemistry using biotin-labeled antibody M-KF and streptavidin-peroxidase (SP).

Example 4: Clinical Study on Antibody M-KF

The study is a phase I clinical trial of multi-center, open and dose escalation. The study evaluates the safety, tolerability, pharmacokinetic (PK) characteristics and preliminary clinical efficacy of antibody M-KF injection in patients with advanced malignant solid tumors, explores maximum tolerated dose (MTD) or maximum administered dose (MAD) and provides recommended doses and reasonable dosing schedules for phase II or follow-up clinical.

The dose escalation study explores safe dose ranges based on a "3+3" dose escalation rule. Stage 1: the 0.01 mg/kg group, the 0.03 mg/kg group and the 0.1 mg/kg group use accelerated titration method to increase the dose; Stage 2: the 0.3 mg/kg group, the 1 mg/kg group, and the 3 mg/kg group are studied in dose escalation according to the standard "3+3" rule.

Three groups adopt an accelerated titration dose escalation plan, that is, cohort size=1. First, one case is included, if no DLT event is observed during the DLT assessment period, they can directly enter the next group for dose escalation. By analogy with this rule ("1+1"), the increase will be accelerated to the (0.1 mg/kg) dose group. If during the accelerated escalation process, once a group has observed a ≥2 level toxic reaction related to the study drug, the accelerated dose escalation should be stopped, and subjects are converted to the standard "3+3" dose escalation (i.e., cohort size=3) rule.

The patient was administered the drug by intravenous infusion for one cycle (treatment course) once every 3 weeks, the infusion duration can be ≥60 min. If the patient has infusion-related reactions and is able to continue treatment, a prophylactic administration of diphenhydramine or acetaminophen could be used based on clinical practice. Treatment was continued until appearance of: disease progression, or withdrawal from intolerable toxicity, or receiving new anti-tumor therapy for non-therapeutic benefit, or withdrawal of informed consent for other reasons, or up to 34 cycles (about 2 years), whichever came first. DLT evaluation period: $1^{st}$ treatment cycle (from the first administration to 21 days after the administration).

The tolerance evaluation indicators relate to: dose-limiting toxicity (DLT) events and their incidence; the safety evaluation indicators relate to: vital signs, physical examination, laboratory examination (routine blood test, blood biochemistry, and thyroid function, coagulation, urinalysis, stool routine, and pregnancy test), electrocardiogram, adverse events (including immune-related adverse events), and the like.

Subjects in all dose groups were required for blood sample collection at specific time points during treatment (first 4 treatment cycles), 2 mL of blood samples were scheduled to be collected at each time point, and the concentration level of the drug in the serum was detected, and the pharmacokinetic (PK) characteristics were studied. PK-related parameters were as follows: parameters include $C_{max}$, $T_{max}$, $T_{1/2}$, CL, Vd, Ke, MRT, $AUC_{(0-\tau)}$ and $AUC_{(0-\infty)}$ at a single administration; the parameters include $C_{max,ss}$, $C_{avg,ss}$, $C_{min,ss}$, $AUC_{(0-\tau),ss}$, $AUC_{(0-\infty),ss}$, $T_{max,ss}$, $T_{1/2,ss}$, CL, Vss, Ke, MRT, accumulation index (Rac), and fluctuation index (DF) at multiple administration.

Evaluation on clinical effectiveness: objective response rate (ORR) is a proportion of subjects in complete response (CR) and partial response (PR). Duration of response (DOR): the time from first assessment of objective response (OR) to first assessment of progressive disease (PD) or any-cause mortality before PD, reflecting the duration of ORR. Progression-free survival (PFS) is the time from the first dose to the appearance of objective progression or all-cause mortality of the tumor (whichever occurred first). "MTD" is the highest dose level of DLT explored in a certain dose group of subjects observed to be ≤1/6 during the DLT evaluation period.

"Dose-limiting toxicity (DLT)" is an adverse event (AE) that occurs during the DLT observation period and is considered to be at least likely related to study drug, specifically as follows:

Hematological Toxicity:

- Grade 4 hematological toxicity;
- Grade 4 thrombocytopenia; Grade 3 thrombocytopenia with bleeding tendency or requiring platelet infusion;
- ≥Grade 3 neutrophilic granulocytopenia with fever;

Non-Hematologic Toxicity:

- Grade 4 non-hematologic toxicity;
- Non-clinical laboratory findings: Grade 3 non-hematologic toxicity including rash, nausea, vomiting, or diarrhea with a duration of >3 days for grade 3;
- Grade 3, 4 non-hematological toxicity from clinical laboratory findings and satisfying one of the following conditions: 1) requiring clinical intervention, 2) abnormalities and resulting in the extent of hospitalization, 3) any drug-related AE that an abnormality persists for more than 1 week resulting in the subject discontinuing treatment at the first cycle, and 4) any drug-related AE that results in treatment being delayed by ≥2 weeks at the second cycle.

The invention claimed is:

1. A method for treating a tumor or cancer, comprising: administering to a patient in need thereof an effective amount of an anti-OX40 antibody or an antigen-binding fragment; wherein the anti-OX40 antibody or the antigen-binding fragment comprises a heavy chain variable region set forth in SEQ ID NO: 7; and the anti-OX40 antibody or the antigen-binding fragment comprises a light chain variable region set forth in SEQ ID NO: 8;

the effective amount of the anti-OX40 antibody or the antigen-binding fragment for each administration is 0.2 mg/kg to 10 mg/kg per treatment cycle by intravenous injection or subcutaneous injection;

one treatment cycle is 1 week, 2 weeks, 3 weeks or 4 weeks; and the tumor or cancer is colorectal cancer.

2. The method according to claim 1, wherein a heavy chain of the anti-OX40 antibody comprises a sequence set forth in SEQ ID NO: 9, or a sequence having at least 95% identity to the sequence set forth in SEQ ID NO: 9; and/or a light chain of the anti-OX40 antibody comprises a sequence set forth in SEQ ID NO: 10, or a sequence having at least 95% identity to the sequence set forth in SEQ ID NO: 10.

3. The method according to claim 1, wherein the anti-OX40 antibody or the antigen-binding fragment has a fucosylation level of 0%-10%.

4. The method according to claim 1, wherein the anti-OX40 antibody or the antigen-binding fragment is expressed by a cell in which an α-(1,6)-fucosyltransferase gene is knocked out.

5. The method according to claim 1, wherein the effective amount of the anti-OX40 antibody or the antigen-binding fragment administered in each treatment cycle is 0.6 mg to 900 mg.

6. The method according to claim 1, wherein the effective amount of the anti-OX40 antibody or the antigen-binding fragment is 0.3 mg/kg to 3 mg/kg per treatment cycle.

7. The method according to claim 1, wherein the effective amount of the anti-OX40 antibody or the antigen-binding fragment is about 0.1 mg/kg, about 0.3 mg/kg, about 1 mg/kg, or about 3 mg/kg per treatment cycle.

8. The method according to claim 1, wherein the effective amount of the anti-OX40 antibody or the antigen-binding fragment administered in each treatment cycle is 10 mg to 600 mg.

9. The method according to claim 1, wherein the effective amount of the anti-OX40 antibody or the antigen-binding fragment administered in each treatment cycle is 10 mg to 250 mg.

10. The method according to claim 1, wherein the effective amount of the anti-OX40 antibody or the antigen-binding fragment administered in each treatment cycle is about 0.6 mg, about 1.8 mg, about 6 mg, about 18 mg, about 60 mg, or about 180 mg.

11. The method according to claim 1, wherein the anti-OX40 antibody or the antigen-binding fragment is administered about once every 1 week, about once every 2 weeks, about once every 3 weeks or about once every 4 weeks.

12. The method according to claim 1, wherein a dose of the anti-OX40 antibody or the antigen-binding fragment for each administration is about 0.3 mg/kg, about 1 mg/kg, or about 3 mg/kg once every 3 weeks.

* * * * *